United States Patent [19]

Furukawa

[11] Patent Number: 4,610,257
[45] Date of Patent: Sep. 9, 1986

[54] PULSE MEASUREMENT SYSTEM
[75] Inventor: Toshio Furukawa, Yamatokoriyama, Japan
[73] Assignee: Sharp Kabushiki Kaisha, Osaka, Japan
[21] Appl. No.: 501,246
[22] Filed: Jun. 6, 1983
[30] Foreign Application Priority Data
Jun. 9, 1982 [JP] Japan ................................ 57-99910
[51] Int. Cl.⁴ ............................................... A61B 5/07
[52] U.S. Cl. ..................................... 128/689; 128/713
[58] Field of Search .............................. 128/680-683, 128/687-690, 672, 677, 713

[56] References Cited
U.S. PATENT DOCUMENTS

| 4,026,277 | 5/1977 | Toda et al. | 128/680 |
| 4,083,366 | 4/1978 | Gombrich et al. | 128/690 |
| 4,159,416 | 6/1979 | Brejnik et al. | 128/690 X |
| 4,331,154 | 5/1982 | Broadwater et al. | 128/677 |
| 4,456,959 | 6/1984 | Hirano et al. | 128/698 X |

FOREIGN PATENT DOCUMENTS 2944157 5/1981 Fed. Rep. of Germany ...... 128/689

Primary Examiner—Kyle L. Howell
Assistant Examiner—Angela D. Sykes
Attorney, Agent, or Firm—Birch, Stewart, Kolasch & Birch

[57] ABSTRACT

Pulse interval data is introduced into a one-chip microcomputer which includes three memory sections A, B and C. The memory section A stores maximum interval data and the memory section C stores minimum interval data. When the new interval data is introduced into the one-chip microcomputer, the new interval data is compared with the maximum data stored in the memory section A or the minimum data stored in the memory section C. When the new interval data is smaller than the maximum interval data and greater than the minimum interval data, the new maximum and minimum interval data is introduced into and stored in the memory sections A and C. The new interval data is then stored in memory section B to satisfy the condition $A \geq B \geq C$. When a predetermined number of sampling operation is completed, the interval data stored in the memory section B shows the central value of the pulse interval.

5 Claims, 6 Drawing Figures

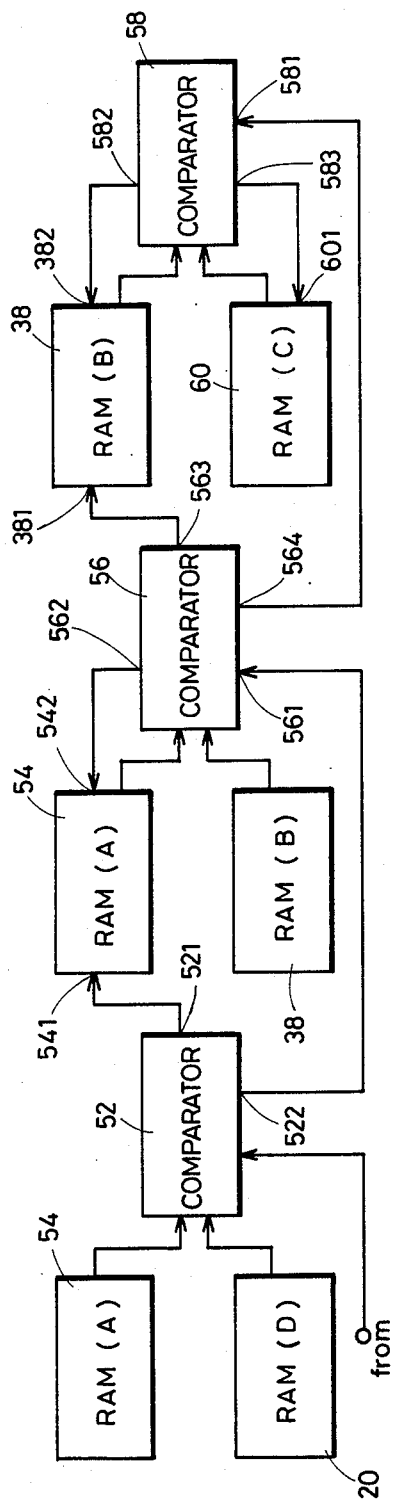
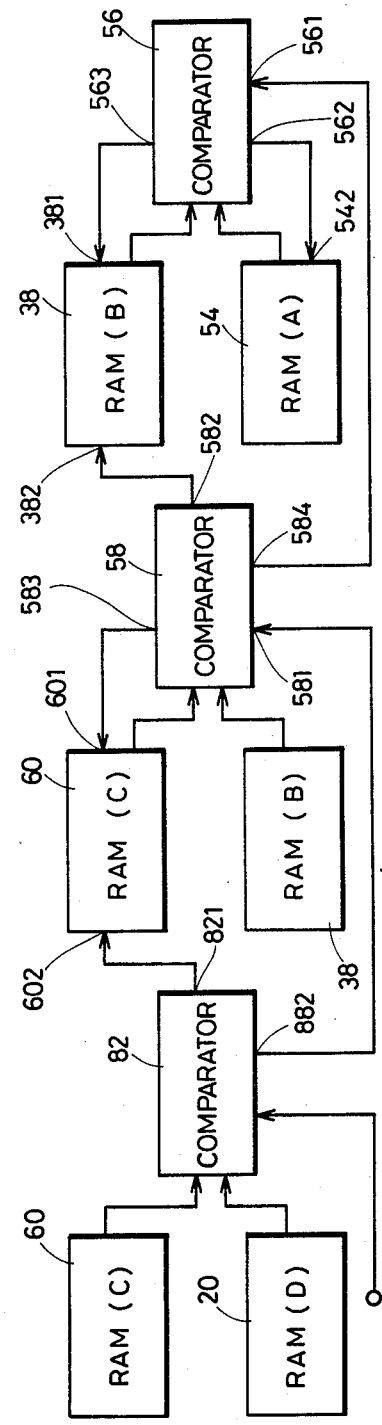

PULSE MEASUREMENT SYSTEM

BACKGROUND AND SUMMARY OF THE INVENTION

The present invention relates to a pulse measurement system and, more particularly, to a pulse number measurement system included in an electronic sphygmomanometer.

Recently, an electronic sphygmomanometer has been developed, which includes a pulse measurement system for measuring a pulse number through the use of pulse interval data derived from the Korotkoff sound detection device. An example of the electronic sphygmomanometer having such a pulse measurement system is disclosed in a copending application Ser. No. 463,475, entitled "ELECTRONIC SPHYGMOMANOMETER WITH VOICE SYNTHESIZER", filed on Feb. 3, 1983 by Ryuichi Miyamae and Haruo Yasuda, and assigned to the same assignee as the present application.

In the conventional pulse measurement system included in the above-mentioned electronic sphygmomanometer, each pulse interval data is stored in a memory (RAM), and the mean interval value is calculated through the use of the thus stored plurality of pulse interval data before obtaining the pulse number information. Accordingly, if the measurement accuracy is desired to be enhanced, the sample number of the pulse interval data stored in the RAM should be increased. Therefore, the conventional pulse measurement system needs a RAM of large memory capacity.

Accordingly, an object of the present invention is to provide a novel pulse measurement system in an electronic sphygmomanometer.

Another object of the present invention is to enhance the measurement accuracy of the pulse number with a memory device of small memory capacity.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a plurality of memory sections are included in a memory device (RAM) for storing the pulse interval data. When new pulse interval data is obtained, the new data is compared with the previously determined maximum interval data or the minimum interval data which have been stored in the RAM. When the new pulse interval data is smaller than the maximum interval data, the previously determined maximum interval data is changed to correspond to the new interval data. When the new pulse interval data is larger than the previously determined minimum data, the minimum data is changed to correspond to the new interval data. The thus updated pulse interval data are used to calculate the pulse number.

In a preferred form, the RAM includes at least three memory sections A, B and C. The memory section A stores the previously determined maximum interval data, and the memory section C stores the previously determined minimum interval data. As already discussed above, the maximum data and the minimum data stored in the memory sections A and C are updated when new pulse interval data is obtained. The memory section B stores the sample data which fulfills the condition $A \geq B \geq C$.

When the pulse interval data has been measured a predetermined number of times, the measurement operation is completed and the sample data stored in the memory section B is used as the center value. That is, the sample data stored in the memory section B is applied to a calculation circuit which calculates the pulse number information.

BRIEF DESCRIPTION OF THE DRAWINGS

The present invention will be better understood from the detailed description given hereinbelow and the accompanying drawings which are given by way of illustration only, and thus are not limitative of the present invention and wherein:

FIG. 5 is a detailed block diagram of a first data processing section included in the equivalent circuit of FIG. 4; and FIG. 6 is a detailed block diagram of a second data processing section included in the equivalent circuit of FIG. 4.

DESCRIPTION OF THE PREFERRED EMBODIMENTS

Figure 1:
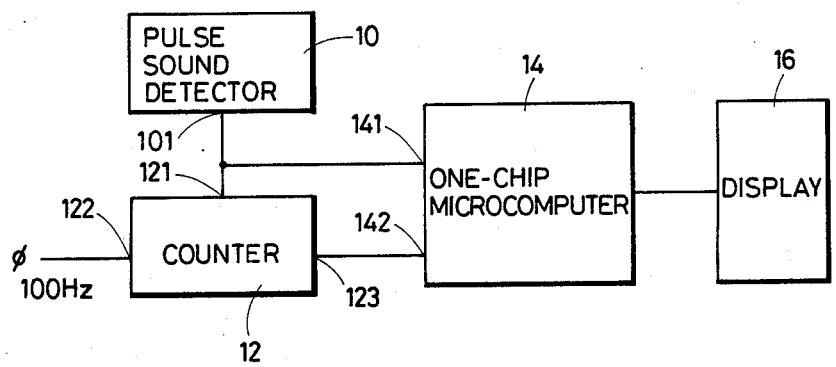
FIG. 1 is a block diagram of an embodiment of a pulse measuring system of the present invention.

FIG. 1 shows an embodiment of a pulse measuring system of the present invention, which comprises a microcomputer control system.

The pulse measuring system of FIG. 1 includes a pulse sound detector 10 (preferably a Korotkoff sound detection circuit associated with a microphone disposed in a cuff), a counter 12, a one-chip microcomputer 14, and a display device 16 for displaying the pulse number measured by the present pulse measuring system.

When the pulse sound is detected by the pulse sound detector 10, a detection pulse signal is developed from an output terminal 101. The detection pulse signal is applied to the counter 12 and the one-chip microcomputer 14 via input terminals 121 and 141, respectively. The counter 12 receives a clock signal of 100 Hz via another input terminal 122. When the detection pulse signal is applied to the input terminal 121, the count contents (count number of the clock signal) stored in the counter 12 are developed from an output terminal 123 of the counter 12 and are applied to the one-chip microcomputer 14 via an input terminal 142. Then, the count contents stored in the counter 12 are cleared to zero for preparing the following count operation. The count contents stored in the counter 12 represent the time interval between two pulses. The one-chip microcomputer 14 includes a calculation circuit for converting the time interval data into the pulse number data. The pulse number information calculated by the one-chip microcomputer 14 is applied to the display device 16 for display purposes. The one-chip microcomputer 14 includes in addition to the calculation circuit, a read only memory (ROM) for storing programs for controlling the system operation, and a random access memory (RAM) for storing the measured data.

Figure 2:
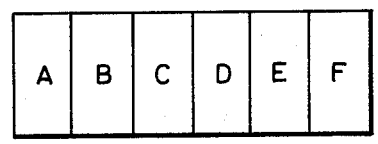
FIG. 2 is a schematic block diagram of a memory device included in the pulse measuring system of FIG. 1.

The random access memory (RAM) included in the one-chip microcomputer 14 has six memory sections A, B, C, D, E and F as shown in FIG. 2. Each memory section has an eight bit construction. The measured pulse interval data are introduced into and stored in the memory sections A, B and C. The pulse interval data are arranged to fulfill the condition $A \geq B \geq C$. The interval data applied from the counter 12 via the input terminal 142 is introduced into and temporarily stored in the memory section D. Furthermore, when the measuring operation is completed, the one-chip microcomputer 14 conducts the calculation to obtain the pulse number data which is introduced into and temporarily stored in the memory section D. The memory section E is a flag to determine as to whether the introduced new data should be compared with the maximum interval data stored in the memory section A or should be compared with the minimum data stored in the memory section C. More specifically, when the flag E="0", the new interval data introduced from the input terminal 142 is compared with the previously determined maximum interval data stored in the memory section A. When the flag E="1", the new interval data introduced into the memory section D is compared with the minimum data stored in the memory section C. The memory section F counts the number of the measuring operation, or the number of the data sampling operation. More specifically, the memory section F conducts the counting operation in response to the detection pulse signal developed from the output terminal 101 of the pulse sound detector 10.

Figure 3:
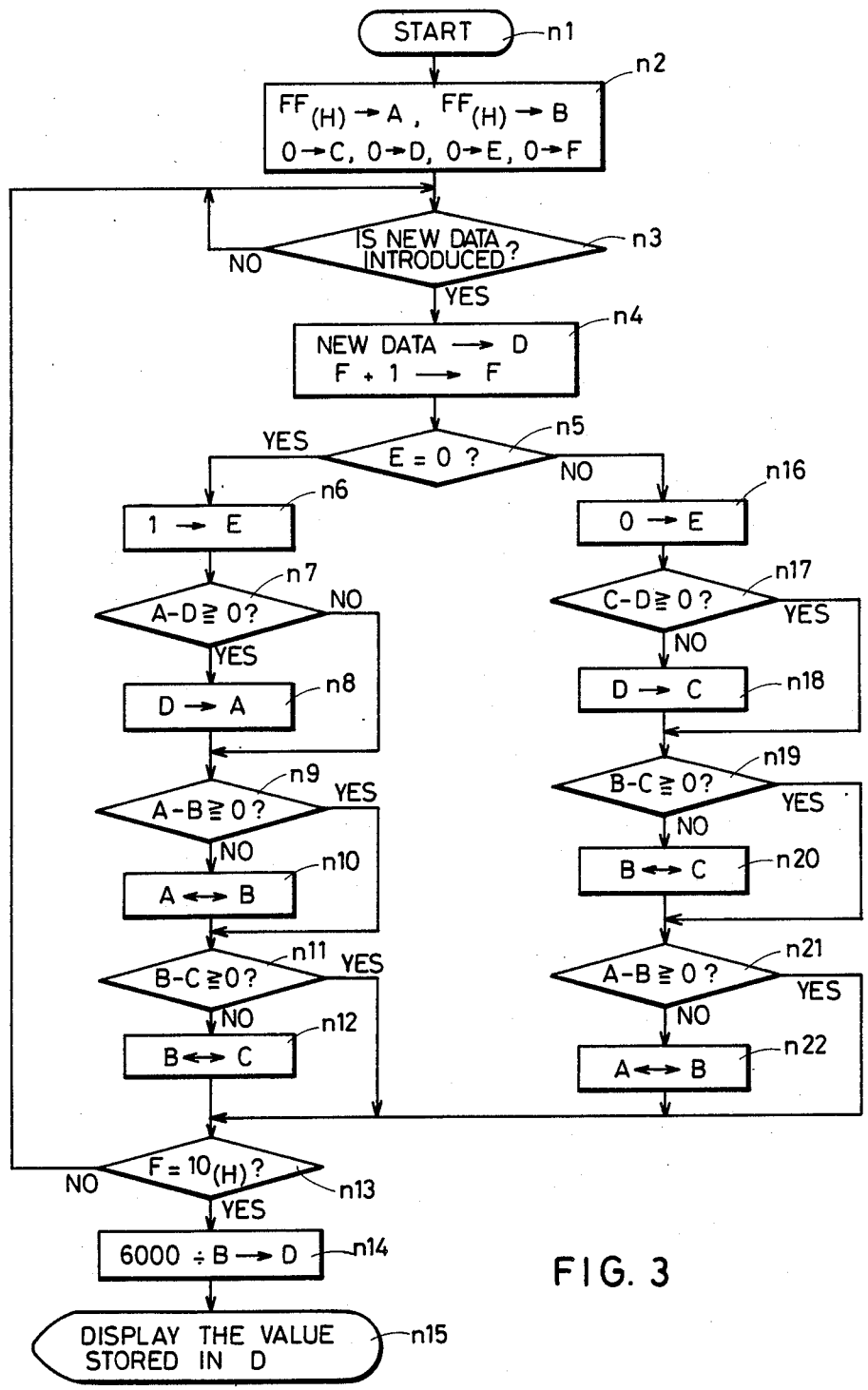
FIG. 3 is a flow chart for explaining an operational mode of the pulse measuring system of FIG. 1.

In a preferred form, the one-chip microcomputer 14 is an "SC 58830" manufactured by Sharp Corporation. An operational mode of the pulse measuring system of FIG. 1 will be described with reference to FIG. 3. The operation of FIG. 3 is controlled by the programs stored in the read only memory (ROM) included in the one-chip microcomputer 14.

At the step n2, the initial setting operation is conducted, wherein the maximum value "$FF_{(H)}$" (H: hexadecimal notation) is introduced into and stored in the memory sections A and B. Furthermore, the minimum value "$00_{(H)}$" is introduced into and stored in the memory sections C, D, E and F. When the new pulse interval data is introduced from the counter 12, the operation is advanced from the step n3 to the step n4 for introducing the new interval data into the memory section D and for increasing the count contents stored in the memory section F by one. At the following step n5, the flag E is checked. When the flag E="0", the new interval data temporarily stored in the memory section D is compared with the maximum interval data stored in the memory section A at the steps n6 through n12. Contrarily when the flag E="1", the new interval data temporarily stored in the memory section D is compared with the minimum interval data stored in the memory section C at the steps n16 through n22.

Now assume that the flag E="0". When the flag E="0" is detected at the step n5, the operation is advanced to the step n6 at which the data "1" is set into the flag E. At the step n7, the new interval data temporarily stored in the memory section D is compared with the maximum interval data stored in the memory section A. When the maximum interval stored in the memory section A is greater than the new interval data temporarily stored in the memory section D($A-D \geq 0$), the operation is advanced to the step n8 at which the new data temporarily stored in the memory section D is introduced into and stored in the memory section A. At the following step n9, the data stored in the memory section A is compared with the data stored in the memory section B in order to arrange the data to fulfill the condition $A \geq B \geq C$. That is, when the interval data stored in the memory section B is greater than the interval data stored in the memory section A, the data stored in the memory sections A and B are changed with each other at the step n10. At the following step n11, the interval data stored in the memory sections B and C are compared with each other. When the time interval data stored in the memory section C is greater than the time interval data stored in the memory section B, the operation is advanced to the step n12 to change the data stored in the memory sections B and C with each other. That is, the new data stored in the memory section D is first compared with the maximum data stored in the memory section A, and the time interval data are arranged to satisfy the condition $A \geq B \geq C$.

When the flag E=1 is detected at the step n5, the new data temporarily stored in the memory section D is compared with the minimum data stored in the memory section C at the step n17. More specifically, at the step n16, the flag E is set to "0" and the operation is advanced to the step n17. When the data stored in the memory section C is smaller than the new data temporarily stored in the memory section D, the operation is advanced to the following step n18 to introduce the new data from the memory section D into the memory section C. At the following step n19, the interval data stored in the memory sections B and C are compared with each other.

When the interval data stored in the memory section B is smaller than the interval data stored in the memory section C, the interval data stored in the memory sections B and C are changed with each other at the following step n20. Then, the operation is advanced to the step n21 to compare the interval data stored in the memory section B with the interval data stored in the memory section A. When the interval data stored in the memory section A is smaller than the interval data stored in the memory section B, the operation is advanced to the step n22 to change the interval data stored in the memory sections A and B with each other. In this way, the data stored in the memory sections A, B and C are arranged to satisfy the condition $A \geq B \geq C$.

The step n13 is provided for checking whether the data sampling operation has been conducted by "$10_{(H)}$" times. If the count contents stored in the memory section F provide a negative answer, the operation is returned to the step n3 to repeat the measuring operation. If an affirmative answer is obtained at the step n13, the operation is advanced to the step n14 where "6000" (since the clock pulse of 100 Hz is applied to the counter 12, one minute (60 seconds) corresponds to 6000 clock pulses) is divided by the interval data stored in the memory section B in order to obtain the pulse number. The thus obtained pulse number is displayed on the display device 16 at the following step n15.

In this embodiment, the time interval data stored in the memory section B is considered as the mean value of the pulse interval when the measuring operation has been conducted by "$10_{(H)}$" times.

Figure 4:
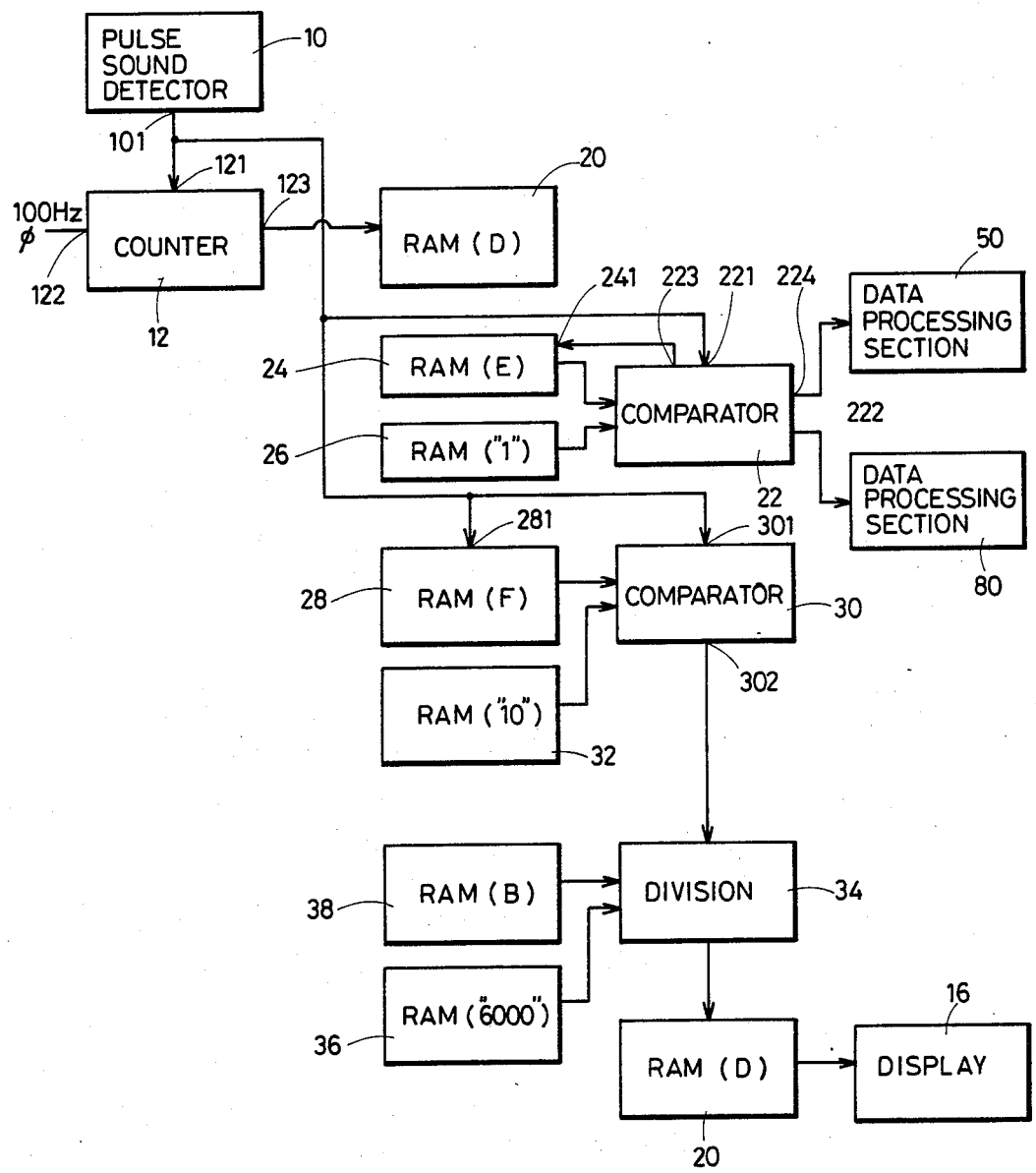
FIG. 4 is a block diagram showing an equivalent circuit of the pulse measuring system of FIG. 1.

FIG. 4 shows an essential part of the pulse measuring system of FIG. 1. Like elements corresponding to those of FIG. 1 are indicated by like numerals. The construction of the one-chip microcomputer 14 will be better understood from the description given hereinbelow.

The time interval data developed from the counter 12 is introduced into a RAM 20 (D) included in the one-chip microcomputer 14. The detection pulse signal developed from the output terminal 101 of the pulse sound detector 10 is applied to a first comparator 22 via an input terminal 221. When the detection pulse signal is applied to the first comparator 22, the first comparator 22 functions to compare the flag data stored in a flag RAM 24 (E) with a fixed data "1" stored in a RAM 26. When the flag data stored in the flag RAM 24 (E) is identical with the data "1" stored in the RAM 26, a coincide detection signal is developed from an output terminal 222 of the first comparator 22, and a data "0" is developed from another output terminal 223 of the first comparator 22 to an input terminal 241 of the flag RAM 24 (E). When the flag data stored in the flag RAM 24 (E) is not identical with the data "1" stored in the RAM 26, discord detection signal is developed from a further output terminal 224 of the first comparator 22. Then, a data "1" is applied from the output terminal 223 to the flag RAM 24 (E) via the input terminal 241. The coincide detection signal developed from the output terminal 222 is applied to a second data processing section 80 which will be described later in detail with reference to FIG. 6. The discord detection signal developed from the output terminal 224 of the first comparator 22 is applied to a first data processing section 50 which will be described later in detail with reference to FIG. 5.

The detection pulse signal developed from the output terminal 101 of the pulse sound detector 10 is further applied to a counter RAM 28 (F) via an input terminal 281 and to a second comparator 30 via an input terminal 301. When the detection pulse signal is applied to the counter RAM 28 (F), the count contents stored therein are increased by one. Then, the count contents stored in the counter RAM 28 (F) are introduced into the second comparator 30 which functions to compare the count contents with a fixed value "10$_{(H)}$" stored in a RAM 32. When the count contents applied from the counter RAM 28 (F) are identical with the fixed value "10$_{(H)}$", the second comparator 30 develops a coincide detection output from an output terminal 302. The coincide detection output developed from the second comparator 30 is applied to a division circuit 34. When the coincide detection output is applied to the division circuit 34, the division circuit 34 conducts the calculation to divide contents ("6000") stored in a RAM 36 by the time interval data stored in a RAM 38 (B). The division results are applied to the RAM 20 (D) for display purposes.

FIG. 5 shows the first data processing section 50. When the discord detection signal developed from the output terminal 224 of the first comparator 22 is applied to a third comparator 52, the comparator 52 functions to compare the interval data stored in a RAM 54 (A) with the new data stored in the RAM 20 (D). When the data stored in the RAM 54 (A) is greater than the new data stored in the RAM 20 (D), the new data stored in the RAM 20 (D) is transferred from the comparator 52 to the RAM 54 (A) via an output terminal 521 and an input terminal 541 for updating the interval data stored in the RAM 54 (A). When the comparing operation at the third comparator 52 is completed, a comparing completion signal is developed from another output terminal 522, which is applied to an input terminal 561 of a fourth comparator 56. When the comparing completion signal is applied to the input terminal 561, the fourth comparator 56 functions to compare the interval data stored in the RAM 54 (A) with the interval data stored in the RAM 38 (B). When the interval data stored in the RAM 38 (B) is greater than or equal to the interval data stored in the RAM 54 (A), the interval data stored in the RAM 38 (B) is developed from an output terminal 562 to an input terminal 542 of the RAM 54 (A), and the interval data stored in the RAM 54 (A) is developed from another output terminal 563 to an input terminal 381 of the RAM 38 (B) in order to change the interval data stored in the RAMs 38 (B) and 54 (A) with each other. When the comparing operation is completed, the fourth comparator 56 develops a comparing completion signal from a further output terminal 564, which is applied to an input terminal 581 of a fifth comparator 58. When the signal is applied to the input terminal 581, the fifth comparator 58 functions to compare the interval data stored in the RAM 38 (B) with the interval data stored in a RAM 60 (C). When the interval data stored in the RAM 60 (C) is greater than or equal to the interval data stored in the RAM 38 (B), the interval data previously stored in the RAM 60 (C) is developed from an output terminal 582 to an input terminal 382 of the RAM 38 (B), and the interval data previously stored in the RAM 38 (B) is developed from another output terminal 583 to an input terminal 601 of the RAM 60 (C) for changing the interval data stored in the RAMs 38 (B) and 60 (C) with each other.

FIG. 6 shows the second data processing section 80. When the coincide detection signal developed from the output terminal 222 of the first comparator 22 is applied to a sixth comparator 82, the comparator 82 functions to compare the interval data stored in the RAM 60 (C) with the interval data stored in the RAM 20 (D). When the interval data stored in the RAM 20 (D) is greater than or equal to the interval data stored in the RAM 60 (C), the interval data stored in the RAM 20 (D) is developed from an output terminal 821 to an input terminal 602 of the RAM 60 (C) in order to update the interval data stored in the RAM 60 (C). When the comparing operation is completed at the sixth comparator 82, a comparing completion signal is developed from another output terminal 822 to the input terminal 581 of the fifth comparator 58. As already discussed above, when the comparing completion signal is applied to the input terminal 581, the fifth comparator 58 performs the comparing operation between the interval data stored in the RAM 38 (B) and the RAM 60 (C). When the interval data stored in the RAM 60 (C) is greater than or equal to the interval data stored in the RAM 38 (B), the interval data previously stored in the RAM 38 (B) is developed from the output terminal 583 to the input terminal 601 of the RAM 60 (C), and the interval data previously stored in the RAM 60 (C) is developed from the output terminal 582 to the input terminal 382 of the RAM 38 (B) for changing the interval data with each other. When the comparing operation is completed at the fifth comparator 58, a comparing completion signal is developed from a further output terminal 584, which is applied to the input terminal 561 of the fourth comparator 56. As already discussed above, in response to the signal applied to the input terminal 561, the fourth comparator 56 functions to compare the interval data stored in the RAMs 54 (A) and 38 (B). When the interval data stored in the RAM 38 (B) is greater than or equal to the interval data stored in the RAM 54 (A), the fourth comparator 56 functions to change the interval data stored in the RAMs 54 (A) and 38 (B) with each other. More specifically, the interval data previously stored in the RAM 38 (B) is developed from the output terminal 562 to the input terminal 542 of the RAM 54 (A) and stored therein. The interval data previously stored in the RAM 54 (A) is developed from the output terminal 563 to the input terminal 381 of the RAM 38 (B) and stored therein. In this way, the interval data are arranged to satisfy the condition $A \geq B \geq C$.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A pulse measurement system comprising:
    pulse detecting means for developing a pulse detection signal when a pulse is detected;
    counter means for counting a time interval between two adjacent pulses and developing pulse interval data;
    first memory means for storing previously determined maximum interval data;
    second memory means for storing previously determined minimum interval data;
    temporary memory means for temporarily storing new interval data developed from said counter means;
    first comparing means for comparing said new interval data with said previously determined maximum interval data stored in said first memory means and applying said new interval data to said first memory means when said maximum interval data is greater than said new interval data derived from said temporary memory means to store updated maximum interval data;
    second comparing means for comparing said new interval data with said minimum interval data stored in said second memory means and applying said new interval data to said second memory means when said new interval data is greater than said minimum interval data to store updated minimum interval data;
    control means for alternately activating said first comparing means and said second comparing means; and
    calculation means for calculating pulse number information in accordance with said updated interval data stored in said first and second memory means.

2. The pulse measurement system of claim 1, further comprising measurement completion detecting means for developing a measurement completion detection signal when said pulse detecting means detects a preselected number of pulses.

3. The pulse measurement system of claim 1, further comprising a display device which displays said pulse number information derived from said calculation means.

4. A pulse measurement system comprising:
    pulse detecting means for developing a pulse detection signal when a pulse is detected;
    counter means for counting a time interval between two adjacent pulses and developing pulse interval data;
    first memory means for storing previously determined maximum interval data;
    second memory means for storing previously determined minimum interval data;
    temporary memory means for temporarily storing new interval data developed from said counter means;
    first comparing means for comparing said new interval data with said previously determined maximum interval data stored in said first memory means and applying said new interval data to said first memory means when said maximum interval data is greater than said new interval data derived from said temporary memory means to store updated maximum interval data;
    second comparing means for comparing said new interval data with said minimum interval data stored in said second memory means and applying said new interval data to said second memory means when said new interval data is greater than said minimum interval data to store updated minimum interval data;
    control means for selectively activating said first comparing means and said second comprising means;
    third memory means for storing intermediate interval data having a data value between the updated maximum interval data stored in said first memory means and the updated minimum interval data stored in said second memory means; and
    calculation means for calculating pulse number information in accordance with said updated interval data stored in said first and second memory means and intermediate interval data stored in said third memory means.

5. The pulse measurement system of claim 4, wherein said counter means is connected to a clock to receive an input signal of 100 Hz, and
    said calculation means comprises a division circuit means for dividing "6000" by said intermediate interval data stored in said third memory means.

* * * * *